United States Patent
Pauly

(10) Patent No.: US 10,176,580 B2
(45) Date of Patent: Jan. 8, 2019

(54) DIAGNOSTIC SYSTEM AND DIAGNOSTIC METHOD

(71) Applicant: SIEMENS HEALTHCARE GMBH, Erlangen (DE)

(72) Inventor: Olivier Pauly, München (DE)

(73) Assignee: SIEMENS HEALTHCARE GMBH (DE)

( * ) Notice: Subject to any disclaimer, the term of this patent is extended or adjusted under 35 U.S.C. 154(b) by 75 days.

(21) Appl. No.: 15/212,366

(22) Filed: Jul. 18, 2016

(65) Prior Publication Data

US 2017/0076451 A1    Mar. 16, 2017

(30) Foreign Application Priority Data

Sep. 11, 2015 (DE) .......................... 10 2015 217 429

(51) Int. Cl.
*G06K 9/00* (2006.01)
*G06T 7/00* (2017.01)
(Continued)

(52) U.S. Cl.
CPC ........ *G06T 7/0014* (2013.01); *G06F 17/3028* (2013.01); *G06F 19/00* (2013.01);
(Continued)

(58) Field of Classification Search
CPC .... G06F 17/3028; G06F 19/00; G06F 19/345; G06K 2209/05; G06K 9/6215;
(Continued)

(56) References Cited

U.S. PATENT DOCUMENTS

2003/0194124 A1* 10/2003 Suzuki .................. G06T 7/0012
382/156
2013/0156267 A1* 6/2013 Muraoka .............. A61B 6/5217
382/103
(Continued)

FOREIGN PATENT DOCUMENTS

CN        101231745 A    7/2008
CN        101520893 A    9/2009
(Continued)

OTHER PUBLICATIONS

Yao, J., O'Connor, S. D., and Summers, R. M., "Automated spinal column extraction and partitioning", in IEEE Int. Symp. Biomed. Imag.: Nano to Macro, Arlington, VA, USA, 390-393 (Apr. 2006).; 2006.

(Continued)

*Primary Examiner* — Tom Y Lu
(74) *Attorney, Agent, or Firm* — Schmeiser, Olsen, & Watts, LLP

(57) ABSTRACT

A first interface for reading a medical patient image record is provided. Furthermore, provision is made of an encoding module for machine-based learning of data encodings of image patterns by an unsupervised deep learning and for establishing a deep-learning-reduced data encoding of a patient image pattern contained in the patient image record. Furthermore, provision is made of a comparison module for comparing the established data encoding with reference encodings of reference image patterns stored in a database and for selecting a reference image pattern with a reference encoding which is similar to the established data encoding. An assignment module serves to establish a key term assigned to the selected reference image pattern and to assign the established key term to the patient image pattern.

(Continued)

Figure 1:
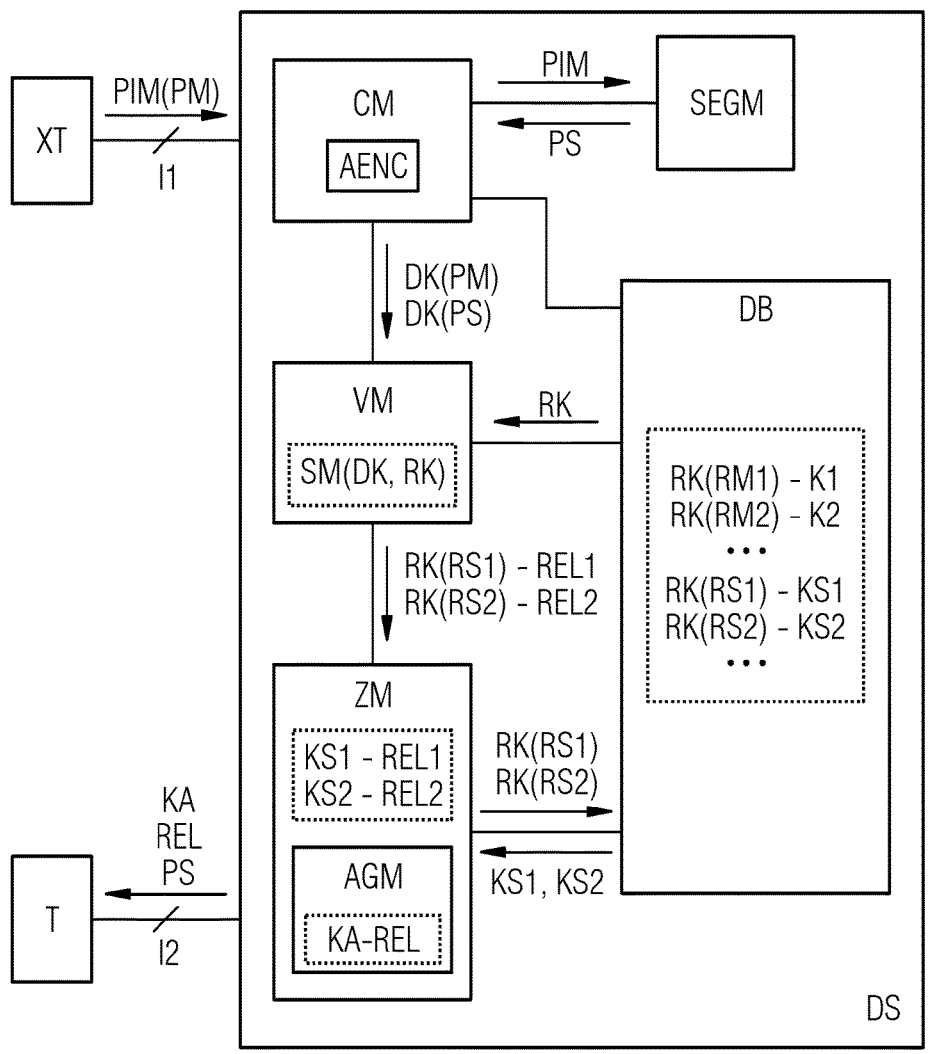

A second interface is provided for outputting the established key term with assignment to the patient image pattern.

14 Claims, 2 Drawing Sheets

(51) Int. Cl.

| | | |
|---|---|---|
| *G06F 17/30* | (2006.01) | |
| *G06K 9/62* | (2006.01) | |
| *G06K 9/66* | (2006.01) | |
| *G06N 99/00* | (2010.01) | |
| *G06T 9/00* | (2006.01) | |
| *G16H 50/20* | (2018.01) | |
| *G06F 19/00* | (2018.01) | |

(52) U.S. Cl.
CPC ......... *G06K 9/6215* (2013.01); *G06K 9/6256* (2013.01); *G06K 9/6269* (2013.01); *G06K 9/66* (2013.01); *G06N 99/005* (2013.01); *G06T 9/00* (2013.01); *G06T 9/002* (2013.01); *G16H 50/20* (2018.01); *G06K 2209/05* (2013.01); *G06K 2209/051* (2013.01); *G06T 2207/20084* (2013.01); *G06T 2207/30012* (2013.01)

(58) Field of Classification Search
CPC ...... G06K 9/6256; G06K 9/6269; G06K 9/66; G06K 2209/051; G06N 99/005; G06T 7/0014; G06T 9/002; G06T 2207/20084; G06T 2207/30012; G06T 7/0081; G06T 9/00; D06F 37/10; D06F 37/02
See application file for complete search history.

(56) References Cited

U.S. PATENT DOCUMENTS

| | | |
|---|---|---|
| 2014/0122515 A1 | 5/2014 | Lee et al. |
| 2015/0110368 A1 | 4/2015 | Solanki et al. |
| 2015/0230773 A1 | 8/2015 | Cho et al. |
| 2016/0174902 A1* | 6/2016 | Georgescu ............... G06T 7/73 600/408 |
| 2016/0300026 A1* | 10/2016 | Bogoni ................ G06F 19/345 |

FOREIGN PATENT DOCUMENTS

| | | |
|---|---|---|
| CN | 102332162 A | 1/2012 |
| CN | 104700118 A | 6/2015 |

OTHER PUBLICATIONS

G. Hinton and R. Salakhutdinov. Discovering binary codes for documents by learning deep generative models. Topics in Cognitive Science, pp. 1-18, 2010.; 2010.

O'Connor, S. D., Yao, J., and Summers, R. M., "Lytic metastases in thoracolumbar spine: Computer-aided detection at CT—preliminary study", Radiology 242, 811-816 (Mar. 2006).; 2006.

Roodman GD (2004), "Mechanisms of bone metastasis". N Engl J, Med 15:1655-1664; 2004.

Theriault RL, "Biology of bone metastases". Cancer Control 19:92-101 (2012); 2012.

Wels M, Kelm BM, Tsymbal A et al, "Multi-stage osteolytic spinal bone lesion detection from CT data with internal sensitivity control.", SPIE Med Imaging Proc 8315, (2012); 2012.

Wiese T, Yao J, Burns JE, Summers RM, "Detection of sclerotic bone metastases in the spine using watershed algorithm and graph cut". SPIE Med Imaging Proc 8315 (2012); 2012.

Kelm, B. Michael, et al. "Spine detection in CT and MR using iterated marginal space learning." Medical image analysis 17.8 (2013): 1283-1292.; 2013.

Yao, J., O'Connor, S. D., and Summers, R., "Computer aided lytic bone metastasis detection using regular CT images", in SPIE Med. Imag.: Image Process., Orlando, FL, USA, 6144, 614459-1-9 (Mar. 2006).; 2006.

Holger R. Roth, Jianhua Yao, Le Lu, James Stieger, Joseph E. Burns, and Ronald M. Summers, "Detection of Sclerotic Spine Metastases via Random Aggregation of Deep Convolutional Neural Network Classifications", MICCAI 2014; 2014.

Hammon et al., "Automatic detection of lytic and blastic thoracolumbar spine metastases on computed tomography", Eur Radiol (2013); 2013.

* cited by examiner

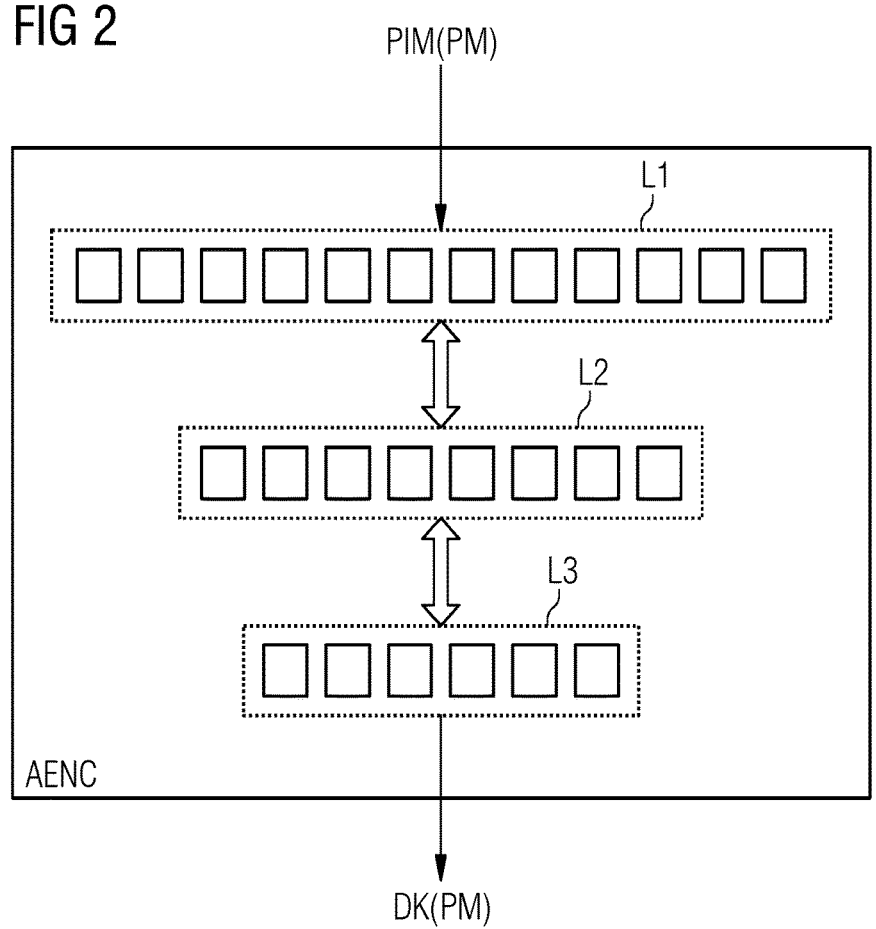

DIAGNOSTIC SYSTEM AND DIAGNOSTIC METHOD

CROSS-REFERENCE TO RELATED APPLICATIONS

This application claims priority to DE Application No. 102015217429.8, having a filing date of Sep. 11, 2015, the entire contents of which are hereby incorporated by reference.

FIELD OF TECHNOLOGY

The following relates to a computer-assisted diagnostic system and diagnostic method for assisting a medical diagnosis.

BACKGROUND

Modern medical diagnostics are assisted to a significant extent by medical imaging which, for example, is based on radiological, angiographic, sonographic and/or tomographic image records of patients. However, evaluating such medical image records by a radiologist was often found to require much outlay. Thus, in order to identify spinal column tumors, the radiologist needs to, in general, examine each individual vertebra imaged in a record of the spinal column. Thus, automatic identification, detection and/or evaluation of anatomical features in medical image records by using image analysis methods is increasingly sought after in order to assist such a diagnosis.

To this end, the use of image analysis methods based upon machine learning is known. These often have a machine classifier, e.g. a so-called random forest classifier, which is specific to the lesions to be identified. However, such classifiers generally require a large training set with manually annotated boundary regions around the lesions to be identified. However, the provision of such manually annotated training sets is very complicated. Moreover, such classifiers often do not take into account a larger visual context about a lesion to be identified in each case, e.g. on the scale of a whole vertebra or the entire spinal column. By way of example, such an image analysis method based on machine classifiers is known from the article "Multi-stage osteolytic spinal bone lesion detection from CT data with internal sensitivity control" by M. Wels, B. M. Kelm, A. Tsymbal et al., in SPIE Med Imaging Proc 8315 (2012).

SUMMARY

An aspect relates to a diagnostic system and diagnostic method, which avoid the aforementioned disadvantages.

In the diagnostic system according to embodiments of the invention for assisting a medical diagnosis, provision is made of a first interface for reading a medical patient image record. The patient image record can be, in particular, an x-ray, ultrasound and/or magnetic resonance record, which represents a planar or volumetric image of an organ or another body structure. Furthermore, the diagnostic system has an encoding module for machine-based learning of data encodings of image patterns by means of unsupervised deep learning and for establishing a deep-learning-reduced data encoding of a patient image pattern contained in the patient image record. A database serves to store a multiplicity of medical reference image patterns with assigned key terms relevant to the diagnosis. Furthermore, provision is made of a comparison module for comparing the established data encoding with reference encodings of reference image patterns stored in the database on the basis of a similarity measure and for selecting a reference image pattern with a reference encoding which is similar to the established data encoding in respect of the similarity measure. An assignment module serves to establish a key term assigned to the selected reference image pattern and to assign the established key term to the patient image pattern. Furthermore, provision is made of a second interface for outputting the established key term with assignment to the patient image pattern.

The method steps to be carried out by the diagnostic system according to embodiments of the invention are the subject matter of the diagnostic method according to embodiments of the invention.

A substantial advantage of embodiments of the invention should be considered that of being able to train the encoding module based on the unsupervised deep learning using unclassified training image patterns as well. In particular, it is possible to dispense with manual specification of features to be identified in many cases. A complicated organ identification by means of an organ model can often be dispensed with in this context.

By assigning key terms to patient image patterns, the latter can be described intuitively in a semantic manner, as a result of which a medical diagnosis can be effectively assisted. In particular, the established key terms can be output with visual assignment to the patient image pattern.

Advantageous embodiments and developments of the invention are specified in the dependent claims.

According to an advantageous embodiment of the invention, the encoding module can comprise a neural autoencoder for establishing the reduced data encoding. Such a neural autoencoder is an artificial neural network which can learn data encodings of input data particularly efficiently.

In particular, the neural autoencoder can comprise an input layer for entering raw image data, low-level image features and/or image features learned by a convolutional neural network. A convolutional neural network is often also referred to as "faltendes neuronales Netz" in German.

Furthermore, the multiplicity of medical reference image patterns can comprise a training set for deep-learning-based training of the encoding module.

Advantageously, the key terms relevant to the diagnosis can specify local properties of an associated reference image pattern and/or image pattern-overarching information about a patient.

According to an advantageous embodiment of the invention, the similarity measure can be a machine-learned similarity measure. Preferably, the similarity measure can be trained on the basis of the same training sets as the encoding module.

In accordance with an advantageous development of the embodiments of the invention, provision can be made of a segmentation module for establishing a position, orientation and/or dimension of organs, organ parts and/or organ regions and for segmenting the patient image record into patient image segments specific to organs, organ parts and/or organ regions. Here, the patient image segments can be considered to be patient image patterns to be encoded. In particular, the segmentation can be carried out in a manner dependent on image patterns learned in a supervised and/or unsupervised fashion. In this way, it is possible to segment the patient image record in the patient image segments which, for example, each represent an individual vertebra of the spinal column or another single anatomical structure. The patient image segments of organs, organ parts and/or organ regions can then be normalized in a segment-specific manner in respect of position, orientation and/or dimension. As a result of this, identification and/or comparison of the relevant anatomical structures can be significantly simplified.

Advantageously, the encoding module can be configured to establish segment-individual data encodings of patient image segments, preferably in a deep-learning-based manner.

Furthermore, the multiplicity of medical reference image patterns with assigned key terms relevant to the diagnosis can comprise a multiplicity of reference image segments with assigned segment-specific key terms. In this way, it is also possible to establish segment-specific key terms on the basis of the reference image patterns. The established segment-specific key terms can be output by the second interface with preferably visual assignment to the relevant patient image segment.

Moreover, the assignment module can be configured to assign a relevance value to the established key term in a manner dependent on the similarity measure between the established data encoding and the reference encoding similar thereto and/or in a manner dependent on the frequency with which this key term is established. The relevance value can be output by the second interface with preferably visual assignment to the assigned key term. In particular, the relevance value can be visualized by the assigned key term itself, e.g. by emboldening or a font size, which is dependent on the relevance value.

Furthermore, provision can be made of an aggregation module for aggregating key terms established for different patient image segments to form an aggregated key term in a manner dependent on the relevance values of these established key terms. In particular, segment-specific key terms can be aggregated for various segments of an organ or organ part to form an aggregated key term for the whole organ or the whole organ part and can be output with preferably visual assignment to this organ or organ part. The aggregated key terms can then form a semantic description for this organ or this organ part. Furthermore, key terms aggregated for various organs, organ parts and/or other patient image segments can be aggregated, in turn, to form one or more superordinate key terms for the patient. The output of the superordinate key terms can be carried out with assignment to the patient as a patient report or as patient findings. The superordinate key terms can then form a semantic description relating to the diagnosis of the patient.

BRIEF DESCRIPTION

Some of the embodiments will be described in detail, with reference to the following Figures, wherein like designations denote like members, wherein:

FIG. 1 shows a diagnostic system and
FIG. 2 shows a layer architecture of a neural autoencoder.

DETAILED DESCRIPTION

FIG. 1 elucidates a diagnostic system DS according to embodiments of the invention for assisting a medical diagnosis on the basis of medical image records of patients. The diagnostic system DS comprises a first interface I1 to a medical image recording device XT, e.g. an x-ray tomography scanner, a magnetic resonance imaging scanner, an ultrasound apparatus or a different recording device, which supplies image records of a body structure of patients. The first interface I1 serves to read medical patient image records from the image recording device XT. In particular, the patient image records can be spatially resolved volumetric images, which are transmitted in the form of image data, e.g. as arrays of voxel values. Below, a patient image record PIM is considered in place of all patient image records.

The patient image record PIM, e.g. a tomographic record of a spinal column, generally comprises a multiplicity of image patterns relevant to the diagnosis, said image patterns representing anatomical structures. Below, the image patterns contained in the patient image record PIM are referred to as patient image patterns. For reasons of clarity, one patient image pattern PM is often considered in place of all patient image patterns.

The diagnostic system DS comprises an encoding module CM with a deep-learning architecture for machine learning of deep-learning-reduced data encodings DK of patient image patterns by means of unsupervised deep learning. In the present exemplary embodiment, the encoding module CM comprises an autoencoder AENC, e.g. a restricted Boltzmann machine. Such a restricted Boltzmann machine is often also referred to as "beschränkte Boltzmann-Maschine" in German. An autoencoder, in this case AENC, serves to learn reduced data encodings of input data in order thus to identify essential patterns and features in the input data and to extract these therefrom. The autoencoder AENC is trained on the basis of a predetermined training set with unclassified input image data. In particular, no manually classified training data are required. The trained autoencoder AENC can thus establish deep-learning-reduced data encodings DK(PM) of the patient image patterns PM contained in the patient image record PIM.

The diagnostic system DS furthermore comprises a segmentation module SEGM coupled to the encoding module CM, for the purposes of establishing a position, orientation and/or dimension of organs, organ parts and/or organ regions and for segmenting the patient image record PIM into patient image segments PS specific to organs, organ parts and/or organ regions. The segmentation is preferably carried out in a manner dependent on image patterns learned in a supervised and/or unsupervised fashion. In this way, it is possible to segment a patient image record of a spinal column into patient image segments which, for example, each represent an individual vertebra.

The individual patient image segments PS can be normalized by the segmentation module SEGM in respect of the established position, orientation and/or dimension in a segment-specific manner. Preferably, the organs, organ parts and/or organ regions can be identified by means of a classifier.

In the present exemplary embodiment, the patient image record PIM is transferred from the encoding module CM to the segmentation module SEGM, segmented there into patient image segments PS and the latter are transferred to the encoding module CM.

Deep-learning-reduced data encodings DK(PS) are established in a segment-individual manner by the autoencoder AENC for the received patient image segments PS and these are transferred from the encoding module CM to a comparison module VM together with the deep-learning-reduced data encodings DK(PM) of the patient image pattern PM.

The diagnostic system DS furthermore comprises a database DB with a multiplicity of stored medical reference image patterns RM1, RM2, . . . , which each have assigned thereto one or more key terms K1, K2, . . . relevant to the diagnosis. Moreover, the database DB has stored therein a multiplicity of reference image segments RS1, RS2, . . . , which each have assigned thereto one or more segment-specific key terms KS1, KS2, . . . . The reference image patterns RM1, RM2, . . . and reference image segments RS1, RS2, . . . can represent, in particular, organs, organ regions and/or organ segments.

The reference image patterns RM1, RM2, . . . with assigned key terms K1, K2, . . . and the reference image segments RS1, RS2, . . . with assigned segment-specific key terms KS1, KS2, . . . comprise, in particular, the training set for the autoencoder AENC and are in each case represented in the database DB by a deep-learning-reduced reference encoding RK. Thus, the reference image pattern RM1 is represented by the reference encoding RK(RM1) thereof, the reference image pattern RM2 is represented by the reference encoding RK(RM2) thereof, the reference image segment RS1 is represented by the reference encoding RK(RS1) thereof, the reference image segment RS2 is represented by the reference encoding RK(RS2) thereof, etc. In the database DB, the key term K1 is assigned to the reference encoding RK(RM1), the key term K2 is assigned to the reference encoding RK(RM2), the segment-specific key term KS1 is assigned to the reference encoding RK(RS1) and the segment-specific key term KS2 is assigned to the reference encoding RK(RS2) in this case.

The comparison module VM coupled to the encoding module CM and the database DB serves to compare the data encodings DK(PM) and DK(PS) established by the encoding module CM with the reference encodings RK of reference image patterns and/or reference image segments stored in the database DB. To this end, reference encodings RK are retrieved from the database DB and compared to the established data encodings DK of the patient image pattern PM and the patient image segments PS on the basis of a similarity measure SM.

The similarity measure SM can be implemented, for example, as a so-called Hamming distance and/or trained by means of supervised and/or unsupervised learning. Preferably, the similarity measure SM can be trained on the basis of the same training set as the training of the autoencoder AENC. The reference image patterns or reference image segments which have a similar reference encoding to the established data encodings DK in respect of the similarity measure SM are selected on the basis of the comparison of the data encodings DK with the reference encodings RK. Preferably, the reference image pattern or reference image segment which is most similar to a respective data encoding DK in respect of the similarity measure SM, for example as a result of a so-called nearest-neighbor search, is selected. For the present exemplary embodiment, the assumption is made that the reference image segments RS1 and RS2 are selected as the reference image segments which are most similar to the patient image segments PS. A relevance value REL1 and REL2 is assigned in each case to the selected reference image segments RS1 and RS2. The relevance values REL1 and REL2 are each dependent on a similarity value based on the similarity measure SM between the reference image pattern RS1 and RS2 and the patient image segments PS and/or dependent on the frequency with which this reference image segment RS1 or RS2 is established.

The selected reference image segments RS1 and RS2 are, in the form of the deep-learning-reduced reference encodings RK(RS1) and RK(RS2) thereof, transmitted from the comparison module VM to an assignment module ZM coupled therewith, in each case with assignment to the established relevance value REL1 and REL2.

The assignment module ZM serves to establish key terms or segment-specific key terms assigned to the selected reference image patterns or reference image segments and to assign the established key terms or segment-specific key terms to the corresponding patient image patterns or patient image segments. In the present exemplary embodiment, the reference encodings RK(RS1) and RK(RS2) of the selected reference image segments RS1 and RS2 are transferred from the assignment module ZM to the database DB coupled thereto in order in this manner to recall the assigned segment-specific key terms KS1 and KS2. Accordingly, the relevance value REL1 is assigned to the segment-specific key term KS1 for the reference image segment RS1 and the relevance value REL2 is assigned to the segment-specific key term KS2 for the reference image segment RS2.

The assignment module ZM comprises an aggregation module AGM for aggregating segment-specific key terms established for different patient image segments PS, in this case KS1 and KS2, to form an aggregated key term KA. This aggregation is carried out in a manner dependent on the relevance values, in this case REL1 and REL2, of the established segment-specific key terms, in this case KS1 and KS2. An aggregated relevance value REL is established by the aggregation module AGM for the aggregated key term KA in a manner dependent on the relevance values REL1 and REL2 and said aggregated relevance value is assigned to the aggregated key term KA.

For the graphical output, the diagnostic system DS comprises a second interface I2 for establishing a connection to a monitor terminal T. The aggregated key term KA with assignment to the aggregated relevance value REL and the patient image segments PS are transferred to the image terminal T by way of the second interface I2. The patient image record PIM is graphically output on the monitor terminal T, wherein the aggregated key term KA and, where applicable, a multiplicity of further aggregated and/or non-aggregated key terms are output with visual assignment to the relevant patient image segment PS. Here, the visual assignment of these key terms can be carried out in such a way that these are placed in the form of so-called tags or as free text over the relevant patient image segment, patient image pattern or otherwise corresponding image position in the patient image record PIM. Preferably, a respective relevance value, in this case REL, can also be output and/or visualized, for example by virtue of the respectively associated key term being output with a font size dependent on the relevance value or with emboldening dependent on the relevance value.

FIG. 2 shows a layer architecture the deep-learning-based autoencoder AENC. In the present exemplary embodiment, the autoencoder AENC comprises three layers L1, L2 and L3 of artificial neurons, which are indicated in FIG. 2 as rectangles within the layers L1, L2 and L3.

The layer L1 serves as the input layer for the autoencoder AENC for entering input data, in this case the patient image record PIM with one or more patient image patterns PM to be identified. Such an input layer of an autoencoder is often also referred to as visible layer. The patient image record PIM can be entered into the input layer L1 in the form of voxel raw data, low-level image features and/or in the form of image features learned by a convolutional neural network. A convolutional neural network is often also denoted CNN. The layer L1 preferably comprises so many artificial neurons that these can represent the entered patient image record PIM with virtually no substantial information losses.

As indicated by a two-dimensional double-headed arrow in FIG. 2, the visible layer L1 is coupled with the layer of L2 acting as a hidden intermediate layer. Such a hidden intermediate layer is often also referred to as intermediate hidden layer. The intermediate hidden layer L2 comprises fewer artificial neurons than the visible layer L1—as indicated by a reduced number of rectangles compared to L1. Accordingly, a learned structure of the intermediate hidden layer L2 represents a correspondingly reduced encoding of the input data, in this case of the patient image record PIM or the patient image features PM.

As indicated by a two-dimensional double-headed arrow, the hidden intermediate layer L2 is coupled to the layer L3. In the present exemplary embodiment, the layer L3 forms an uppermost hidden layer of the autoencoder AENC. Such an uppermost hidden layer is often also referred to as top hidden layer. The layer L3 comprises fewer artificial neurons than the hidden intermediate layer L2, which is indicated in FIG. 2 by a reduced number of rectangles within the layer L3. The layer L3 uses the reduced encodings learned by the layer L2 as input data and forms more strongly reduced or compressed encodings therefrom. Accordingly, the learned structure in layer L3 represents a significantly reduced, and therefore compressed, data encoding DK of the input data, in this case of the patient image record or the patient image patterns PM. The compressed data encoding DK formed by the layer L3 is output by the autoencoder AENC.

For the purposes of further data reduction, the autoencoder AENC can by all means have further hidden layers.

The autoencoder AENC is trained by unsupervised deep learning. By way of example, this can be carried out by virtue of attempts being made to reconstruct the input data from the layer L1 from the structure of the layer L3. Then, the autoencoder AENC is trained to the extent that the reconstruction result deviates as little as possible from the input data.

Below, a typical application context of embodiments of the invention is described within the scope of spinal column diagnostics. By way of example, a computed tomography record of the spinal column serves as a patient image record. The spinal column record is automatically parsed by means of machine learning methods and a patient report or patient findings, with a semantic description of each vertebra or of parts thereof by means of a set of key terms relevant to the diagnosis, are generated therefrom. The key terms can comprise local properties of a respective vertebra, such as e.g. a visual appearance of a specific lesion, the size and the position thereof within a vertebra and assigned diagnostic information such as type, severity and/or malignancy of the lesion. Moreover, the keywords can also comprise vertebrae-overarching information, which characterize the spinal column and/or the patient, such as e.g. specifications about the stage of the disorder or specifications in respect of the therapy selection. Furthermore, the keywords can also be subdivided in respect of specific aspects, such as e.g. keywords relating to a diagnosis, keywords relating to a position and/or keywords relating to a visual appearance. A set of keywords established according to embodiments of the invention can form a semantic description of the patient image record, optionally with the assigned relevance values. This semantic description can lead to the automatic generation of a patient report in order thus to assist a radiologist with his diagnosis.

Compact data encodings for each vertebrae type, an associated similarity measure for comparing data encodings and a database with reference encodings of individual vertebrae and/or individual vertebra regions are provided for implementing embodiments of the invention. Keywords relevant to the diagnosis are assigned to the reference encodings. Since the deep-learning-based encoding model does not require training data classified in advance, it is also possible, in a simple manner, to provide large training sets with a multiplicity of vertebrae regions and corresponding key terms, for example by resorting to available patient image records with associated findings. A training set provided in this manner can then be used to learn low-dimensional data encodings of vertebrae regions, possibly to learn the similarity measure and to fill the database with reference encodings of vertebrae regions.

In order to carry out the method, the patient image record of the spinal column is parsed in a first step in order to detect all vertebrae contained therein. For the detected vertebrae, the position, orientation and dimensions thereof are acquired. This detection or acquisition can be carried out by means of machine learning methods, e.g. by means of so-called marginal space learning.

A boundary region is preferably defined for a respectively detected vertebra and/or vertebra region, said boundary region delimiting the relevant vertebra or vertebra region from other image patterns. An image segment with the respective vertebra and/or vertebra region is subsequently transformed in such a way that the position, the orientation and/or a dimension of the vertebra or vertebra region is normalized. A specific patient image segment, e.g. a computed tomography partial volume, is output for the respective vertebra or vertebra region as a result of this preprocessing step.

In a further, optional step, each vertebra and/or vertebra region is segmented into a set of overlapping sub-regions, which form a further set of patient image segments.

The patient image segments of the vertebrae, vertebrae regions and/or vertebrae sub-regions are encoded into a learned low-dimensional encoding by means of the autoencoder AENC. By way of example, the encoding can be based on volumetric intensity values of a computed tomography record. For encoding purposes, the patient image segments of the vertebrae are fed to the input layer L1 of the autoencoder AENC. The neural activity of the input layer L1 induced thereby propagates through the neural network of the autoencoder AENC to the topmost hidden layer L3 via the layer L2. The state of the neurons in the layer L3 induced hereby supplies a binary code for a respectively input patient image segment. This binary code can serve as reduced low-dimensional encoding for the image pattern identified in the patient image segments. The autoencoder AENC can be trained in advance by means of a large training set with unclassified computed tomography data, without using a content of key terms. Subsequently, particularly important key terms relevant to the diagnosis can be subdivided according to the content thereof and hence it is possible to carry out a supervised back-propagation method in order to fine-tune the neural network of the autoencoder AENC.

By means of the data encodings of the patient image segments established by the autoencoder AENC, a data query system is able to query those reference image segments which are as similar as possible to the patient image segments in respect of the similarity measure. To this end, it is preferably possible to undertake a so-called nearest neighbor query. The segment-specific key terms assigned to the most similar reference image segments are then assigned to the relevant patient image segments.

A set of vertebrae-specific key terms, which describe the relevant vertebrae as a whole, can be generated on the basis of segment-specific key terms, which were generated for various sub-regions of a vertebra, and on the basis of the relevance values and/or frequencies thereof.

Moreover, the key terms generated for the vertebrae sub-regions and/or the vertebrae as a whole can be generated to describe the spinal column as a whole or to describe the patient in order thus to supply patient findings for the current examination. By way of example, it is possible, to this end, to output a short list of vertebrae with assigned key terms relevant to the diagnosis, a complete list of the vertebrae together with e.g. three of the most relevant and/or most frequent key terms, a keyword histogram for each vertebra and/or a keyword cloud for each vertebra.

Although the present embodiments of has been disclosed in the form of preferred embodiments and variations thereon, it will be understood that numerous additional modifications and variations could be made thereto without departing from the scope of the invention.

For the sake of clarity, it is to be understood that the use of 'a' or 'an' throughout this application does not exclude a plurality, and 'comprising' does not exclude other steps or elements.

The invention claimed is:

1. A computer-assisted diagnostic system for assisting a medical diagnosis, comprising:
   a) a patient image record reader, wherein said patient image record reader is used for reading a patient image record,
   b) a machine-based learning encoding module, wherein said machine-based learning encoding module is used for data encodings of image patterns by unsupervised deep learning using unclassified training image patterns, and for establishing a deep-learning-reduced data encoding of a patient image pattern contained in the patient image record,
   c) a medical reference image pattern database, wherein said database for storing a multiplicity of medical reference image patterns with assigned key terms relevant to the medical diagnosis,
   d) an image pattern comparison module, wherein said comparison module is used for comparing the established data encoding with reference encodings of reference image patterns stored in the database on the basis of a similarity measure and for selecting a reference image pattern from the medical reference image patterns with a reference encoding which is similar to the established data encoding in respect of the similarity measure,
   e) a key term assignment module, wherein said assignment module is for establishing a key term assigned to the selected reference image pattern and for assigning the established key term to the patient image pattern, and
   f) a key term output, wherein said key term output is assigned to the patient image pattern.

2. The diagnostic system as claimed in claim 1, wherein the machine-based learning encoding module comprises a neural autoencoder for establishing the reduced data encoding.

3. The diagnostic system as claimed in claim 2, wherein the neural autoencoder comprises an input layer for entering raw image data, low-level image features and/or image features learned by a convolutional neural network.

4. The diagnostic system as claimed in claim 1, wherein the multiplicity of medical reference image patterns comprises a training set for deep-learning-based training of the encoding module.

5. The diagnostic system as claimed in claim 1, wherein the key terms relevant to the diagnosis specify local properties of an associated reference image pattern and/or image pattern-overarching information about a patient.

6. The diagnostic system as claimed in claim 1, wherein the similarity measure is a machine-learned similarity measure.

7. The diagnostic system as claimed in claim 1, further comprising a segmentation module for establishing a position, orientation and/or dimension of organs, organ parts and/or organ regions and for segmenting the patient image record into patient image segments specific to organs, organ parts and/or organ regions.

8. The diagnostic system as claimed in claim 7, wherein the machine-based learning encoding module is configured to establish segment-individual data encodings of patient image segments.

9. The diagnostic system as claimed in claim 7 wherein the reference image patterns with assigned key terms relevant to the diagnosis comprises a multiplicity of reference image segments with assigned segment-specific key terms.

10. The diagnostic system as claimed in claim 1, wherein the assignment module is configured to assign a relevance value to the established key term in a manner dependent on the similarity measure between the established data encoding and the reference encoding similar thereto and/or in a manner dependent on a frequency with which this key term is established.

11. The diagnostic system as claimed in claim 10, wherein an aggregation module (AGM) for aggregating key terms established for different patient image segments to form an aggregated key term (KA) in a manner dependent on the relevance values of the established key terms.

12. A computer-assisted diagnostic method for assisting a medical diagnosis, wherein
   a) a patient image record is read,
   b) data encodings of image patterns are learned by machine by means of unsupervised deep learning using unclassified training image patterns, and a deep-learning-reduced data encoding of a patient image pattern contained in the patient image record is established,
   c) the established data encoding is compared to reference encodings of stored medical reference image patterns on the basis of a similarity measure, wherein key terms relevant to the diagnosis are assigned to the medical reference image patterns,
   d) a reference image pattern from the medical reference image patterns with a reference encoding similar to the established data encoding in respect of the similarity measure is selected,
   e) a key term assigned to the selected reference image pattern is established and assigned to the patient image pattern, and
   f) the established key term is output with assignment to the patient image pattern.

13. A computer program product, comprising a non-transitory computer readable hardware storage device having computer readable program code stored therein, said program code configured to execute a diagnostic method as claimed in claim 12 or to implement a diagnostic system.

14. A computer-readable storage medium, comprising a stored computer program product stored on a non-transitory computer storage medium as claimed in claim 13.

* * * * *